US007838045B2

(12) United States Patent
Ribnicky et al.

(10) Patent No.: US 7,838,045 B2
(45) Date of Patent: Nov. 23, 2010

(54) **ANTI-INFLAMMATORY ACTIVITY OF PHENETHYLISOTHIOCYANATE (PEITC) AND THE *BARBAREA VERNA* SEED PREPARATION CONTAINING THIS COMPOUND**

(76) Inventors: David M. Ribnicky, 1005 Route 28, North Branch, NJ (US) 08876; Moul Dey, 11 Kearny Ave., 1B, Edison, NJ (US) 08817; Ilya Raskin, 48 Alexander Rd., Manalapan, NJ (US) 07726

( * ) Notice: Subject to any disclaimer, the term of this patent is extended or adjusted under 35 U.S.C. 154(b) by 0 days.

(21) Appl. No.: 11/506,672

(22) Filed: Aug. 18, 2006

(65) Prior Publication Data

US 2007/0042061 A1   Feb. 22, 2007

Related U.S. Application Data

(60) Provisional application No. 60/709,148, filed on Aug. 18, 2005.

(51) Int. Cl.
*A61K 36/00* (2006.01)
(52) U.S. Cl. ........................................ 424/725; 424/776
(58) Field of Classification Search ........................ None
See application file for complete search history.

(56) References Cited

U.S. PATENT DOCUMENTS 5,589,154 A * 12/1996 Anderson ................... 424/1.41
6,348,220 B1   2/2002 Ribnicky et al.
2002/0061352 A1   5/2002 Ekanayake et al.

OTHER PUBLICATIONS

Vickers et a.: A Vaccine Vagainst Alzheimer'S Disease.: Drugs Aging.: 2002. 19 (7) pp. 487-494.*
Clohisy et al.: Direct Inhibition of NF-Kb Blocks Bone Erosion Associated With Inflammatory Arthritis.: The Journal of Immunology.: 2003. 171: 5547-5553.*
Gerhauser et al.: Mechanism-Based In Vitro Screening of Potential Cancer Chemopreventive Agents.: Mutation Research.: 523-524. 2003. 163-172.*
Krakauer. Molecular Therapeutic Targets in Inflammation: Cyclooxygenase and NF-kB. Current Drug Targets-Inflammation & Allergy. 2004. 3. pp. 317-324.*
Rose et al., B-Phenylethyl and 8-methylsulphinyloctyl isothiocyanates, constituents of watercress, suppress LPS induces production of nitric oxide and prostaglandin E2 in RAW 264.7 macrophages, Nitric Oxide, Jun. 2005, vol. 12 No. 4 pp. 237-243, especially p. 237 and p. 240.
Krakauer, T., "Molecular Therapeutic Targets in Inflammation: Cyclooxygenase and NF-kappaB", Current Drug Targets—Inflammation & Allergy, vol. 3, pp. 317-324, (2004).
Heiss et al., "Nuclear Factor kappaB Is a Molecular Target for Sulforaphane-mediated Anti-inflammatory Mechanism", The Journal of Biological Chemistry, vol. 276, No. 34, pp. 32008-32015, (2001).

Sporn et al., "Peptide Growth Factors and Inflammation, Tissue Repair, and Cancer", The Journal of Clinical Investigation, vol. 78, pp. 329-332, (1986).
Hooper et al., "Prevention of Experimental Allergic Encephalomyelitis by Targeting Nitric Oxide and Peroxynitrite: Implications for the Treatment of Multiple Sclerosis", PNAS, vol. 94, No. 6, pp. 2528-2533, (1997).
Simonian et al., "Oxidative Stress in Neurodegenerative Diseases", Annual Review, vol. 36, pp. 83-106, (1996).
Hantraye et al., "Inhibition of Neuronal Nitric Oxide Synthase Prevents MPTP-induced Parkinsonism in Baboons", Nature Medicine, vol. 2, No. 9, pp. 1017-1021, (1996).
Ohshima et al., "Chronic Infections and Inflammatory Processes as Cancer Risk Factors: Possible Role of Nitric Oxide in Carcinogenesis", Mutation Research/Fundamental and Molecular Mechanisms of Mutagenesis, vol. 305, Issue 2, pp. 253-264, (1994).
Esposito et al., "The Metabolic Syndrome and Inflammation: Association or Causation?", Nutr. Metab. Cardiovasc. Dis.,vol. 14, pp. 228-232, (2004).
Stoewsand, G.S., "Bioactive Organosulfur Phytochemicals in Brassica oleracea Vegetables—A Review", Fd. Chem. Toxic, vol. 33, No. 6, pp. 537-543, (1995).
Chen et al., "Suppression of Inducible Nitric Oxide Production by Indole and Isothiocyanate Derivatives from BrassicaPlants in Stimulated Macrophages" , Planta Med, vol. 69, pp. 696-700, (2003).
Gerhauser et al., "Mechanism-based In Vitro Screening of Potential Cancer Chemopreventive Agents", Mutation Research, vols. 523-524, pp. 163-172, (2003).
Martin et al., "Protective Effect of the Interleukin-1 Receptor Antagonist (IL-Ira) on Experimental Allergic Encephalomyelitis in Rats", Journal of Neuroimmunology, vol. 61, pp. 241-245, (1995).
Brooks, P., "Use and Benefits of Nonsterodial Anti-Inflammatory Drugs", Am. J. Med., vol. 3A, pp. 9S-13S, (1998).
Baldwin, Jr., A.S., "The NF-kappaB and IkappaB Proteins: New Discoveries and Insights", Annu. Rev. Immunol., vol. 14, pp. 649-681, (1996).
Baum, et al., "Utilization of Nonsteroidal Antiinflammatory Drugs", Arthritis & Rheumatism, vol. 26, Issue 6, pp. 686-692, (1985).
Pathak et al., "Oxidative Stress and Cyclooxygenase Activity in Prostate Carcinogenesis: Targets for Chemopreventive Strategies", European Journal of Cancer, vol. 41, pp. 61-70, (2005).
Bombardier et al., "Comparison of Upper Gastrointestinal Toxicity of Rofecoxib and Naproxen in Patients with Rheumatoid Arthritis", The New England Journal of Medicine, pp. 1520-1528, (2000).

(Continued)

*Primary Examiner*—Patricia Leith
*Assistant Examiner*—Melenie McCormick
(74) *Attorney, Agent, or Firm*—Marshall, Gerstein & Borun LLP

(57) ABSTRACT

The subject of this invention is the anti-inflammatory activity of a formulation of *Barbarea verna* (upland cress, early winter cress, or winter cress) seed preparation (BSP) containing phenethylisothiocyanate as its main active ingredient. BSP is a promising anti-inflammatory agent, which can be used for treatment of many inflammation-related conditions, including but not limited to rheumatoid and osteoarthritis, acute and chronic pains, lupus, irritable bowl disease, cancer and metabolic syndrome.

2 Claims, No Drawings

OTHER PUBLICATIONS

Juni et al., "COX 2 Inhibitors, Traditional NSAIDs, and the Heart", BMJ, 330: pp. 1342-1343, (2005).

Ribnicky et al., "Seed of *Barbarea verna* as a Rich Source of Phenethyl Isothiocyanate to Provide Natural Protection from Environmental and Dietary Toxins", Journal of Nutraceuticals, Functional & Medical Foods, vol. 3, No. 3, pp. 43-65, (2001).

Harris et al., "Comparative Effects of Phenethylisothiocyanate (PEITC) and an Extract of Upland Cress (*Barbarea verna*) Seed on Intestinal Tumorigenesis In Vivo", Abstract for the Annual Meeting of the American Association for Cancer Research, Anaheim, California, (2005).

Mosmann, T., "Rapid Colorimetric Assay for Cellular Growth and Survival: Application to Proliferation and Cytotoxicity Assays", Journal of Immunological Methods, vol. 65, pp. 55-63, (1983).

von Knethen et al., "Superinduction of Cyclooxygenase-2 by NO and Agonist Challenge Involves Transcriptional Regulation Mediated by AP-1 Activation", Biochemistry, vol. 39, pp. 1532-1540, (2000).

von Knethen et al.., "NF-kappaB and AP-1 Activation by Nitric Oxide Attenuated Apoptotic Cell Death in RAW 264.7 Macrophages", Molecular Biology of the Cell, vol. 10, pp. 361-372, (1999).

Wu et al., "Hypoxia Induces Myocyte-dependent COX-2 Regulation in Endothelial Cells" Role of VEGF, Am. J. Physiol. Heart Circ. Physiol, vol. 285, pp. H2420-H2429, (2003).

Baeuerie et al., "NF-kappaB: Ten Years After", Cell, vol. 87, pp. 13-20, (1996).

Yamamoto et al., "Role of the NF-kappaB Pathway in the Pathogenesis of Human Disease States", Current Molecular Medicine, vol. 1, pp. 287-296, (2001).

Oshima et al., "Suppression of Intestinal Polyposis in Apc 716 Knockout Mice by Inhibition of Cyclooxygenase 2 (COX-2)", Cell, vol. 87, pp. 803-809, (1996).

Kwon et al., "Effects of Aspirin on Nitric Oxide Formation and De Novo Protein Synthesis by RINm5F Cells and Rat islets", Molecular Pharmacology, vol. 52, pp. 398-405, (1997).

Pfaffl, M.W., "A New Mathematical Model for Relative Quantification in Real-time RT-PCT", Nucleic Acids Research, vol. 29, No. 9, pp. 2002-2007, (2001).

Rodriguez et al., "Risk of Upper Gastrointestinal Bleeding and Perforation Associated with Individual Non-steroidal Anti-inflammatory Drugs", The Lancet, vol. 343, Issue 8900, pp. 769-772, (1994).

Sheng et al., "Modulation of Apoptosis and Bcl-2 Expression by Prostaglandin E2 in Human Colon Cancer Cells", Cancer Research, vol. 58, pp. 362-366, (1998).

Steinbach et al., "The Effect of Celecoxib, a Cyclooxygenase-2 Inhibitor, In Familial Adenomatous Polyposis", The New England Journal of Medicine, vol. 342, No. 26, pp. 1946-1952, (2000).

Subbaramaiah et al., "Inhibition of Cyclooxygenase: A Novel Approach to Cancer Prevention", Experimental biology and Medicine, vol. 216, pp. 201-210, (1997).

Takahashi et al., "Increased Expression of Inducible and Endothelial Constitutive Nitric Oxide Synthases in Rat Colon Tumors Induced by Azoxymethane", Cancer Research, vol. 57, pp. 1233-1237, (1997).

Karin et al., "Phosphorylation Meets Ubiquitination: The Control of NF-kappaB Activity", Annual Review of Immunology, vol. 18, pp. 621-663, (2000).

Graziewicz et al., "Nitric Oxide Inhibits DNA Ligase Activity: Potential Mechanisms for NO-Mediated DNA Damage", Carcinogenesis, vol. 17, No. 11, pp. 2501-2505, (1996).

Clements, P., "Nonsteroidal Anti-Inflammatory Drugs (NSAISs)", Textbook of Rheumatology, 4th Edition, pp. 700-730, (1981).

Ben-Av et al., Induction of Vascular Endothelial Growth Factor Expression in Synovial Fibroblasts by Prostaglandin E and Interleukin-1: A Potential Mechanism for Inflammatory Angiogenesis, FEBS Letters, vol. 372, pp. 83-87, (1995).

Callejas et al., "Selective Inhibitors of Cyclooxygenase-2 Delay the Activation of Nuclear Factor kappaB and Attenuate the Expression of Inflammatory Genes in Murine Macrophages Treated with Lipopolysaccharide", Molecular Pharmacology, vol. 63, No. 3, pp. 671-677, ((2003).

Firestein, G.S., Starving the Synovium: Angiogenesis and Inflammation in Rheumatoid Arthritis, The Journal of Clinical Investigations, vol. 103, No. 1, pp. 3-4, (1999).

Wong et al., "Inducible Nitric Oxide Synthase Gene Expression in the Brain During Systemic Inflammation", Nature Medicine, vol. 2, pp. 581-584, (1996).

Langman, M.J., "Ulcer Complications and Nonsteroidal Anti-inflammatory Drugs", Am. J. Med., vol. 84, No. 2A, pp. 15-19, (1988).

Ji, R., "Perpheral and Central Mechanisms of Inflammatory Pain, with Emphasis on MAP Kinases", Current Drug Targets—Inflammation and Allergy, vol. 3, pp. 299-303, (2004).

Goodwin et al., "Regulation of the Immune Response by Prostaglandins", Journal of Clinical Immunology, vol. 3, No. 4, pp. 295-315, (1983).

Kroncke et al., "Inducible Nitric Oxide Synthase in Human Disease", Clin. Exp. Immunol., vol. 113, pp. 147-156, (1998).

Hecht, S., "Tobacco and Cancer: Approaches Using Carcinogen Biomarkers and Chemoprevention", Ann NY Acad. Sci., vol. 83, pp. 91-111, (1997).

Whelton et al., "Nonsteroidal Anti-inflammatory Drugs: Effects on Kidney Function", J. Clin. Pharmacol., vol. 31, pp. 588-598, (1991).

\* cited by examiner

ANTI-INFLAMMATORY ACTIVITY OF PHENETHYLISOTHIOCYANATE (PEITC) AND THE *BARBAREA VERNA* SEED PREPARATION CONTAINING THIS COMPOUND

CROSS REFERENCE TO RELATED APPLICATION

This application claims the benefit of U.S. Provisional Patent Application No. 60/709,148 filed Aug. 18, 2005, the entirety of which is hereby incorporated by reference into this application.

FIELD OF THE INVENTION

The present invention relates to therapeutic compositions and methods for treating inflammation and for preventing the dysfunctional conditions that are provoked by inflammatory mediators such as enzymes and cytokines.

BACKGROUND OF THE INVENTION

Inflammation is a host response to infection and injury. Inflammatory cells respond to foreign substances and inflammatory stimuli by producing bioactive mediators such as prostanoids, cytokines and chemokines that interact with many cell types to amplify the inflammatory response (Krakauer, 2004, Curr. Drug Targets-Inflammation and allergy 3(3): 317-324). Deregulation of these processes leads to acute and chronic inflammatory diseases for which pharmacological intervention is necessary to attenuate cellular inflammation pathways.

Chronic inflammation and infections lead to the up-regulation of pro-inflammatory enzymes like iNOS and COX2, which are responsible for elevated levels of NO (nitric oxide) and prostaglandins (PGs), respectively. Aberrant production or overproduction of NO has been implicated in the pathogenesis of cancer via reactive nitrogen oxide species-mediated reactions (Heiss et al., 2001, J Biol Chem 276(34): 32008-32015; Sporn and Roberts, 1986, J Clin Invest 78:329-332). PGs have a role as pro-inflammatory mediators.

The pro-inflammatory enzymes are involved in the pathogenesis of many chronic diseases including multiple sclerosis (MS), Parkinson's disease, Alzheimer's disease, and colon cancer (Oshima et al., 1996, Mutat. Res. 305:253-264; Takahashi et al., 1997, Cancer Res 57:1233-1237; Hooper et al., 1997, Proc Natl Acad Sci USA 94: 2328-2333; Simonian and Coyle, 1997, Annu Rev Pharmacol Toxicol 36: 83-106; Hantraye et al., 1996, Nat Med 2: 1017-1021). iNOS plays an important role in the inflammatory response of tissues to injury and infectious agents. Chronic inflammation, carcinogenesis, and metabolic syndrome are thought to be mechanistically linked (Ohshima and Bartsch 1994, Mutat. Res 305: 253-264; Esposito and Giugliano 2004).

PEITC, an organo-sulfur bio-active compound, has many well-documented cancer chemo-preventive properties, the most significant one being the anti-carcinogenic effects to tobacco smoke. Its anti-cancer activities have been demonstrated in humans as well as in different animal models (Stoewsand, 1995, Food Chem Toxicol 33:537-43; Heiss et al., 2001, J Biol Chem 276:32008-32015; Chen et al., 2003, Planta Med 69:696-700; Gerhauser et al., 2003, Mutat Res 523-524:163-172, Rose et al. 2005, Nitric Oxide 12:237-243.)

Pro-inflammatory cytokines like interleukin-1-β (IL1β) are mediators in the pathogenesis of many chronic inflammatory diseases including rheumatoid arthritis (RA), a classic example of autoimmune disorder (Martin et al., 1995, J. Neuroimmunol 61:241). It plays a significant role in destructive processes, in synovitis and cartilage destruction. Chronic inflammation may represent a triggering factor in the origin of metabolic syndrome: stimuli such as over-nutrition, physical inactivity and aging would result in cytokine (like IL1β) hypersecretion and eventually lead to insulin resistance and diabetes in genetically or metabolically predisposed individuals (Esposito and Giugliano 2004). The occurrence of metabolic syndrome is highly prognostic of future risk of cardiovascular events.

Non-steroidal anti-inflammatory drugs (NSAIDs) are among the most widely prescribed and used drugs for rheumatologic as well as non-rheumatologic conditions (Brooks 1998; Clements and Paulus, 1981, in Textbook of Rheumatology 4th Ed; 700-730). More than 1% of the U.S. population uses these drugs on a daily basis. Worldwide, more than 30 million people consume NSAIDs daily (Baum et al., 1985, Arthritis Rheum 28: 686-692).

Characterization and use of effective anti-inflammatory agents are important issues for public health. Almost every known NSAID has moderate to severe side-effects of various kinds. NSAIDs such as Aspirin inhibit the activity of both constitutive COX1 and inducible COX2. Consequently they can cause platelet dysfunction, gastrointestinal ulceration and renal damage, since COX1 helps to maintain normal physiological functions such as mucus production in the gastric mucosa (Pathak et al., 2005, Eur J Cancer 41(1):61-70). For this reason, selective COX2 inhibitors, such as celecoxib and rofecoxib had been more attractive as anti-inflammatory as well as potential chemopreventive agents, although their potential toxicities were never disregarded (Bombardier et al., 2000, N Engl J Med 343(21):1520-1528). Mounting evidence suggests a cardio-protective effect of COX2 and potential detrimental effects of COX2 inhibitors on the heart (Wu et al., 2003, Am J Physiol Heart Circ Physiol 285(6):H2420-2429). The safety issue of drugs containing COX2 inhibitors has become a matter of widespread controversy (Juni et al., 2005, BMJ 330: 1342-1343).

The serious ramifications from inflammation and inflammation-related diseases are clear. Yet, drugs in use to treat these conditions have secondary harmful or potentially harmful effects. What is needed is new therapeutic products that exert anti-inflammatory effect through different metabolic pathways than the present drugs, thus avoiding the known negative side effects.

SUMMARY OF THE INVENTION

The inventive concept pertains to anti-inflammatory activities discovered for phenethylisothiocyanate (PEITC), and for a PEITC-containing formulation of *Barbarea verna* seed preparation (BSP) to treat and prevent inflammatory related conditions.

Accordingly, in a first aspect, the invention features a method for treating an inflammation-related disorder in a mammal comprising the step of administering to a subject a therapeutically effective amount of phenethylisothiocyanate. In preferred embodiments of the above method, the disorder is selected from the group consisting of rheumatoid arthritis, asthma, inflammatory bowel disease, Crohn's disease, ulcerative colitis, multiple sclerosis, psoriasis and skin rushes, chronic obstructive pulmonary disease, allergic rhinitis, cardiovascular disease, lupus, and metabolic syndrome; the phenethylisothiocyanate is administered orally; the administered phenethylisothiocyanate is a formulation of a plant preparation; and the plant preparation is *Barbarea verna* seed preparation. In a particularly preferred embodiment, the plant preparation is *Barbarea verna* seed fortified with essential oil of *Barbarea verna* seed.

In a second aspect, the invention features a composition comprising phenethylisothiocyanate, wherein the phenethylisothiocyanate is prepared from a seed preparation fortified with seed essential oil.

In a third aspect, the invention features a pharmaceutical composition for the treatment of an inflammatory condition in a mammal comprising phenethylisothiocyanate.

In preferred embodiments, the seed preparation comprises ground seed soaked in aqueous liquid; the seed preparation is obtained from a plant of the family Brassicaceae; and the composition comprises a preparation of *Barbarea verna* seed that has been fortified with the essential oil of *Barbarea verna* seed. In other preferred embodiments, the composition further comprises a pharmaceutically acceptable excipient or carrier; and the composition is in a form that can be administered orally.

In preferred embodiments, the composition comprises a preparation of winter cress seed fortified with essential oil of winter cress seed.

As used herein, "anti-inflammatory" refers to a statistically significant and detectable or measurable reduction in inflammation (e.g., induced inflammation) that is observed in individuals that have been treated with an anti-inflammatory composition in accordance with the invention, relative to individuals that have not been similarly treated. Typically, inflammation is induced in an individual, and the individual is then treated with an anti-inflammatory composition of the invention. Inflammation is then measured at a time period (e.g., after about 1 hour or more) subsequent to induction of inflammation and treatment (if any) with the anti-inflammatory compositions of the invention.

As used herein, the term "inflammation" is a localized tissue response characterized by, but not limited to, increased blood flow, increased temperature (including, but not limited to, fever), redness, swelling, and/or pain.

As used herein, by "a therapeutically effective amount" is meant an amount of a composition comprising the anti-inflammatory product that is sufficient to reduce, decrease, and/or inhibit an inflammatory response in an individual. In an alternative embodiment, the term "therapeutically effective amount" refers to an amount of a composition comprising the anti-inflammatory product that is sufficient to alleviate, ameliorate, prevent, and/or eliminate at least one symptom known to be associated with a condition and/or the pathology of a condition involving an inflammatory response.

DETAILED DESCRIPTION OF THE INVENTION

Unless defined otherwise, all technical and scientific terms used herein have the same meaning as is commonly understood by one of skill in the art to which this invention belongs. All publications and patents referred to herein are incorporated by reference.

Some foods contain compounds capable of providing health benefits beyond the basic nutritional needs of the body. However, the amounts consumed as food often are insufficient to produce any clinical effect. One such example is winter cress, which contains phenethylisothiocyanate (PEITC). PEITC, an organo-sulfur bio-active compound, has many well-documented cancer chemo-preventive properties, the most significant being the anti-carcinogenic effects to tobacco smoke. PEITC is present in various amounts in many herbaceous plants belonging to the Brassicaceae family. Of these *Barbarea verna*, winter cress, is the richest source of PEITC ($PhCH_2CH_2N=C=S$) (Ribnicky et al., 2001, J. Nutraceuticals, Functional and Med. Foods 3: 43-65).

BSP is a preparation of winter cress seed that has been fortified with the essential oil of winter cress seed and therefore contains higher amounts of PEITC than seed preparation that has not been fortified. A non-fortified seed preparation is described in U.S. Pat. No. 6,348,220. In previous studies, BSP containing 7.8% PEITC as primary active molecule according to GC-MS profile, was shown to have cancer chemo-preventive properties (Ribnicky et al., 2001, J. Nutraceuticals, Functional and Med. Foods 3: 43-65; Harris et al., 2005, "Comparative effects of phenethyl isothiocyanate (PEITC) and an extract of winter cress (*Barbarea verna*) seed on intestinal tumorigenesis in vivo." Abstract for the Annual Meeting of the American Association for Cancer Research, Anaheim, Calif.).

A study was conducted to test and evaluate the anti-inflammatory properties of BSP as compared to known anti-inflammatory agents. The results of the evaluation establish that BSP is a potent anti-inflammatory agent with numerous medicinal uses. Those results are discussed in more detail below.

The invention contemplates a botanical formulation containing PEITC that can be utilized to treat inflammatory conditions. The formulation has a pronounced anti-inflammatory effect in an animal model of inflammation. Previously, BSP as well as synthetic PEITC were not known to inhibit the LPS-mediated induction of IL1β, which is a positive marker for inflammation and immune suppression. Results of the studies detailed here illustrate that PEITC affects the IL1β marker.

In view of the findings reported herein, PEITC is a valuable therapeutic for the prevention and/or treatment of inflammation and related inflammatory-diseases. PEITC delivered as a composition comprising BSE is also contemplated. Accordingly, example embodiments of efficacious compositions of the present invention for the control of inflammation and conditions related thereto are provided.

The dosage of active ingredient in the compositions of this invention may be varied, however, it is necessary that the amount of the active ingredient be such that a suitable dosage form is obtained. The selected dosage depends upon the desired therapeutic effect, on the route of administration, and on the duration of the treatment.

The compositions of the present invention can be administered by any mode known in the art. Such modes include, for example, oral, nasal, topical (including buccal and sublingual) or parenteral (including subcutaneous, intramuscular, intravenous and intradermal) administration.

For ease to the patient, oral administration is preferred. However, as practiced by those skilled in the art, other routes of administration may be necessary. Thus, depending upon the condition, a skilled artisan can determine which form of administration is best in a particular case for balancing the dose needed versus periodic delivery.

Solid dosage forms for oral administration can include, for example, capsules, tablets, pills, powders, tinctures and granules. The solid dosage forms can include an admixture with food and chewable forms. In such solid dosage forms, the active compound is admixed with at least one inert pharmaceutically acceptable carrier such as sucrose, lactose, or starch. Such dosage forms can also comprise additional substances such as lubricating agents, for example, magnesium stearate. In the case of capsules, tablets and pills, the dosage forms can also comprise buffering agents. Tablets and pills can additionally be prepared with enteric coatings. In the case of chewable forms, the dosage form can comprise flavoring agents.

A pharmaceutical composition, nutraceutical, or cosmetic composition, is also contemplated, comprising an effective amount of PEITC to treat inflammatory or autoimmune diseases or to prevent and treat conditions associated with inflammation, such as skin aging. In one embodiment, pharmaceutical compositions of the present invention comprise a pharmaceutically effective amount of PEITC or a derivative or a pharmacologically active analog or a structurally related compound that modulates inflammation and a pharmaceutically acceptable carrier to control an inflammatory condition. A therapeutically effective amount will be determined dependent upon recognized variables such as age and weight of the subject; the particular route of administration and the particular condition.

Pharmaceutically acceptable preparations for parenteral administration include sterile, aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. The active therapeutic ingredient may be mixed with excipients that are pharmaceutically acceptable and are compatible with the active ingredient. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like.

A typical treatment course may comprise administration of multiple doses on a daily basis of a composition comprising an amount of an anti-inflammatory extract product effective to inhibit an inflammatory response in an individual. Such a treatment course may be continued for significant periods of time, for example, three doses per day over three months or even indefinitely.

Of course, the foregoing are only exemplary treatment schedules, and other schedules are contemplated. In each case, the suitability of such schedules and the aforementioned modes of administration are determined by those of skill in the art, using routine procedures. For example, those of skill in the art will be able to take the information disclosed in this specification and optimize treatment regimes for human subjects based on clinical trials performed in accordance with the specification.

In one embodiment, a therapeutically effective dose is contemplated as within a range of 0.1 mg/kg to 200 mg/kg.

Nutraceutical compositions comprising PEITC, as described above, and one or more nutraceutical-acceptable formulation agents are also encompassed by this invention.

In one embodiment, the pharmaceutical composition, nutraceutical, functional food or topical composition, as described above, comprises an effective amount of PEITC to treat inflammatory and autoimmune diseases including but not limited to rheumatoid arthritis, asthma, inflammatory bowel disease, Crohn's disease, ulcerative colitis, multiple sclerosis, psoriasis and skin rashes, chronic obstructive pulmonary disease, allergic rhinitis, cardiovascular disease, lupus, and metabolic syndrome or to prevent and treat conditions associated with inflammation, such as skin aging, for example.

An animal model of inflammation, rat paw edema, was used to gauge the effectiveness of the composition in vivo. Further, the effect on pro-inflammatory gene expression (COX-2, iNOS, and IL1β) and nitric oxide production in LPS-elicited RAW macrophages was measured to determine possible modes of action.

Carrageenan, a sulfated polysaccharide, promotes inflammation by activating pro-inflammatory cells. Carrageenan-induced inflammation in the rodent paw presents a classical model of edema formation and hyperalgesia and has been extensively used in the development of nonsteroidal anti-inflammatory drugs and selective COX2 inhibitors (as described in Krakauer 2004).

Because PEITC is the main active component of BSP, the effect of synthetic PEITC was compared with that of BSP. BSP significantly reduced pre-established paw edema in rats. This in vivo anti-inflammatory effect is consistent with the results of in vitro quantitative RT-PCR studies demonstrating the inhibition of LPS-mediated induction of iNOS, COX2, and IL1β transcription by BSP. When tested against various forms of synthetic isothiocyanates and two commonly used anti-inflammatory drugs in in vitro studies, PEITC and BSP were more effective.

BSP or its derivatives, or other plant preparation preparations of PEITC are established as an efficacious drug for the prevention and treatment of inflammation-related diseases.

It will be appreciated that the treatment methods of the invention are useful in the fields of human medicine and veterinary medicine. Thus, the subject or individual to be treated may be a mammal, preferably human, or other animals. For veterinary purposes, subjects include, for example, farm animals such as cows, sheep, pigs, horses, and goats; companion animals such as dogs and cats; exotic and/or zoo animals; laboratory animals including mice, rats, rabbits, guinea pigs, and hamsters; and poultry such as chickens, turkeys, ducks, and geese. A related aspect of the invention provides a use for the biologically active compositions or compounds in preparing medicaments for the treatment or prevention of the disorders disclosed herein.

The compositions (and thus the methods) of the invention can be used alone or in conjunction with other therapies including, for example, administration of other therapeutic agents (including other anti-inflammatory compositions or formulations).

EXPERIMENTAL

Statistical Analysis

In all cases (Tables 1, 2) except the in vitro data on Aspirin and rofecoxib, values are expressed as the mean (±standard error). The significance of the difference between the means (percentage change in paw size) of the untreated and the BSP treated groups of rats (samples) was determined by students' t-test as described by Press et al. (Press et al., (1992), Numerical recipes, 2nd ed. Cambridge, UK: Cambridge University Press). $p \leq 0.05$ was considered significant (Table 4).

Example 1

Chemicals and Biochemicals

PEITC with 99% purity, various other forms (phenyl, tertiary-butyl, allyl, isopropyl) of isothiocyanates (Table 4), antibiotics, Acetyl salicylate (Aspirin) and LPS were purchased from Sigma Chemicals (St. Louis, Mo.). All other chemicals, including cell culture media and PCR enzymes were obtained from either, Invitrogen Inc., USA or Stratagene Inc., (Lajolla, Calif.). For rofecoxib, the content of a Vioxx™ 25 mg capsule was dissolved in 95% ethyl alcohol to prepare a stock solution of 10 mg/ml. Winter cress seeds were obtained from Alf Christiansen Seed Co., Mount Vernon, Wash. RAW 264.7 cell line (ATCC TIB-71) was provided by American Type Culture Collection, VA.

Example 2

Preparation of BSP

BSP is a preparation of *Barbarea verna* (winter cress) seed that has been fortified with the essential oil of winter cress seed and, therefore, contains higher amounts of PEITC than seed that has not been fortified. For the production of BSP, 200 g of finely ground winter cress seed was soaked with 100 ml of distilled water. The wet material was thinly spread on a disposable aluminum tray (230 cm×280 cm) and floated in a covered water bath at 37° C. for 20 min followed by lyophilization to a final temperature of 18° C.

PEITC essential oil was extracted by hydro-distillation of ground winter cress seed for 4-5 h with a modified Clevenger apparatus. Generally, 200 g of ground seed plus 1 L of distilled water would yield 1-2 ml of essential oil after hydro-distillation. This process was repeated to produce larger quantities of oil.

In order to fortify the seed mixture, 22 g of essential oil, containing at least 95% PEITC, was dissolved in 100 ml of 95% ethanol and added to the dried seed material described above and mixed until the moisture was evenly distributed. After the seed mixture was evenly spread into the aluminum tray (230 cm×280 cm), the ethanol was evaporated in a fume hood for 6-8 hours. The resulting dried material was defined as BSP and the PEITC content was measured to be 7.8% by a GC-MS method described in U.S. Pat. No. 6,348,220.

For analysis of the dried material, 1 g of BSP was dissolved into 50 ml of ethyl acetate and particulates were removed. Samples were injected into a GC-MS (model 5890/5971, Hewlett-Packard mass spectrometer equipped with a 30-m× 0.25 mm DB-5MS fused silica capillary column (J&W Scientific, Folsom Calif.). Chromatographic parameters were as follows: injection temperature at 150° C., initial oven temperature at 50° C. for 5 min followed by a ramp at 30° C./min to 280° C. for 3 min. The MS was operated in the scanning mode from 50 to 650 (m/z). The retention time of PEITC was 11.3 min and appeared as the primary compound that was extracted. The major ion of PEITC has a mass of 91 (m/z) and molecular ion of mass 163 (m/z). The abundance of these ions and the integration value of the entire peak were used together with standard curves created from a PEITC chemical standard to quantify the PEITC concentration in BSP.

Example 3

Rat Paw Edema Anti-Inflammatory Assay

Adult male Wistar rats (100-200 g) were used throughout this study. Fifteen rats, five per cage, were housed in a room maintained at a constant temperature with 12-hour light/dark cycle at 24-26° C. and had free access to food and water. Animals were handled as soon as possible to reduce the stress of physical manipulation. Before experimentation, animals had one week to adapt to the conditions of the facility. Prior to the start of the experiment body weights were measured individually to determine the dose for the treatment and animals were randomly divided into three different groups of five rats.

The paw edemas were induced for 1 hour by subcutaneous injection of 100 μl of 1% solution of lambda carrageenan (Sigma Inc., USA) (w/v solution in saline, 0.9% NaCl) in the plantar aponeurosis of the right hind paw, followed by treatment. The edemas were measured by volume displacement method using a digital plethysmometer (Ugo Basile, Italy) prior to (basal volume) and 3, 5, 24 and 48 hours after the treatment. PEITC (in its concentrated oil form extracted by hydro-distillation of ground winter cress seed as described earlier in this section) or Aspirin (Sigma Inc., USA) was administered orally at 200 mg/kg body weight and an equal volume of the vehicle (4% apricot kernel balm) was given to the control group. Time dependent rat paw size reduction reflected the anti-inflammatory effect of the specific treatment. The increase in volume and the percentage change (Table 1) caused by the irritant was estimated after subtracting the basal volume of the paw before injection. A lower percent (%) numerical value would indicate a stronger anti-inflammatory activity.

In the paw edema experiment in rats, the induction of inflammation was allowed to develop for one hour after the carrageenan injection before treatment with PEITC essential oil (PEO, see method). Aspirin, a known NSAID, was used as a positive control. A group, treated only with vehicle, was considered as untreated control. It was observed that the effect of PEO was as quick and effective as Aspirin when given at the same doses (Table 1). In both PEO and Aspirin treated groups, the paw sizes were about half way back to normal, as compared to untreated group, after 3 hours. In the 2 hours following that period, the treatments were still very active, showing a further sharp decline of the paw sizes in both the PEO and Aspirin-treated groups. The observations at 3 and 5 hours, showed a statistically significant difference (p [t-test]=0.0) in paw sizes between PEO and the untreated group. Up to the 5th hour no significant healing in the untreated group was observed.

TABLE 1

Effect of PEO on carrageenan-induced rat paw edema.

| Time after treatment (carageenan injection 1 hour before treatment) | % paw size increase in Aspirin-treated group(1) | % paw size increase in PEO-treated group(2) | % paw size increase in un-treated group(3) | t-test* probability for similarity of means (d.f = 8) between groups (2) & (3) |
|---|---|---|---|---|
| 3 hours | 23.91 ± 10.15 | 26.19 ± 6.21 | 52.27 ± 7.16 | 0.00* |
| 5 hours | 8.77 ± 8.14 | 9.97 ± 9.53 | 49.07 ± 7.20 | 0.00* |
| 24 hours | 7.72 ± 5.47 | 10.13 ± 13.16 | 26.93 ± 11.94 | 0.05* |
| 48 hours | 0.18 ± 7.56 | −2.44 ± 10.56 | 4.98 ± 8.04 | 0.22 |

*p (t-test) probability gives the significance of the observed difference between sample means. $p \leq 0.05$, is considered significant

Example 4

Cell Culture Assay

The mouse monocyte/macrophage cell line RAW 264.7 (obtained from American Type Culture Collection, ATCC, VA USA) was maintained in Dulbecco's Modified Eagle Medium (DMEM) (Invitrogen Inc) supplemented with 100 U/ml penicillin, 100 µg/ml streptomycin, and 10% heat-inactivated fetal calf serum. All incubations were at 37° C. in a 5% $CO_2$ in internal air atmosphere, within the growth chamber.

Cells were seeded at a density of $0.4 \times 10^6$ cells per well (viable cell counts performed with a hemocytometer), in 24 well plates 12 hours prior to treatment. The cells were then treated with test compounds at required concentrations (predetermined doses) for 2 hours before elicitation with LPS at 1 µg/ml for an additional 6 hours. For every experiment one positive control (cells treated only with LPS) and one negative control (cells without any treatment) were included. For treatments and the controls, two replicates were made in each case. At the end, cells were harvested in Trizol reagent (Invitrogen Inc) for subsequent cellular RNA extraction. The stock of BSP used for the assay was prepared by partially dissolving 50 mg/ml seed preparation in 95% ethyl alcohol for 15 minutes by sonication, where it released PEITC in the clear supernatant that was used for the cell treatment. Cell viability was measured by MTT assay (Mosmann (1983) J. Immunol. Methods 65:55-63).

Example 5

Total RNA Extraction Purification and cDNA Synthesis

Total RNA was extracted from RAW macrophages using Trizol reagent (Invitrogen Inc.) following manufacturer instructions. RNA was quantified spectro-photometrically by absorption measurements at 260 nm and 280 nm using Nano-Drop™ system (NanoDrop Technologies Inc. DE, USA). RNA was assessed qualitatively by gel-electrophoresis methods. RNA was then treated with DnaseI (Invitrogen Inc.) also following manufacturer guidelines, to remove any traces of DNA contamination. The cDNAs were synthesized using 3 µg of RNA for each sample using Stratascript™ Reverse Transcriptase, an RNA dependent DNA polymerase (Stratagene, La Jolla, Calif.), following manufacturer protocol. Utmost care was taken to minimize any quantification inaccuracy and pipetting error.

Example 6

Quantitative Polymerase Chain Reaction (qPCR) and Data Analysis

The synthesized cDNAs were diluted 4-fold. 2 µl of each of these diluted samples were used for PCR reactions of 25 µl final volume. The other components of the PCR reactions were 0.5 µl of 6 µM gene specific primers (oligos synthesized by IDT Inc. USA), 12.5 µl of Brilliant SYBR green PCR master mix (2×) (Stratagene, La Jolla, Calif.) containing green jump-start Taq ready mix. ROX (Stratagene, La Jolla, Calif.) was used as an internal dye. To avoid interference due to genomic DNA contamination, only intron-overlapping primers were selected using the software Primer Express™ (Applied Biosystem, Foster City, Calif.) as follows:

| | |
|---|---|
| β-actin-F: | 5'-AACCGTGAAAAGATGACCCAGAT-3' |
| β-actin-R: | 5'-CACAGCCTGGATGGCTACGT-3' |
| COX2-F: | 5'-TGGTGCCTGGTCTGATGATG-3' |
| COX2-R: | 5'-GTGGTAACCGCTCAGGTGTTG-3' |
| iNOS-F: | 5'-CCCTCCTGATCTTGTGTTGGA-3' |
| iNOS-R: | 5'-TCAACCCGAGCTCCTGGAA-3' |
| IL1β-F: | 5'-CAACCAACAAGTGATATTCTCCATG-3' |
| IL1β-R: | 5'-GATCCACACTCTCCAGCTGCA-3' |

Forward and reverse pairs of the primers are indicated above as "F" and "R" respectively. PCR amplifications were performed on MX3000p system (Stratagene, La Jolla, Calif.) using 1 cycle at 50° C. for 2 min, 1 cycle of 95° C. for 10 minutes, followed by 40 cycles of 15 seconds at 95° C. and 1 min at 60° C. The dissociation curve was completed with one cycle of 1 minute at 95° C., 30 seconds of 55° C. and 30 seconds of 95° C. NRT (non-RT control) and NTC (no template control) were included in the PCR program as quality control steps.

RNA expressions for COX2, iNOS and IL1β, normalized with respect to the expression of housekeeping β-actin gene, were analyzed using the ΔΔCt method (software from Stratagene inc, USA) as described by Pfaffl (Pfaffl, 2001, Nucleic Acids Res 29(9):2002-2007). The ΔΔCt values obtained from these analyses were converted [(1−ΔΔCt)×100] to obtain percentage of inhibition (% inhibition or % downregulation) which reflected the anti-inflammatory properties of the test compounds (Table 2, 4). A value of 100% indicates complete inhibition of LPS-stimulated genetic up-regulation. 0% implies absence of any anti-inflammatory activity of the test compound. Negative % inhibition suggests a genetic up-regulation caused by the specific treatment in excess to LPS stimulation and are interpreted as "up-regulation" (Table 4).

The in vitro experiments were designed to quantify the relative amount of transcripts for target genes within the total RNA in individual cell batches undergoing dose-dependent treatments with BSP, synthetic PEITC, Aspirin, rofecoxib and four other forms of isothiocyanates (phenyl, ter-butyl, allyl, isopropyl). Since experiments were started with equal number of cells for each treatment, the change in relative mRNA quantity is indicative of the effect of the particular treatment. Also, for each assay, two control sets were monitored. The positive control (treated only with LPS), showed the maximum up-regulation of the marker genes. The negative control (received no treatment), maintained a constant amount of transcripts for all constitutively expressed genes and served as a reference baseline. Monitoring the expression of β-actin, a constitutively expressed housekeeping gene, also served as a quality control step for determining RNA degradation during the course of the assay.

The in vitro experiments showed BSP to be highly anti-inflammatory in assays with all three target genes-iNOS, IL1β and COX2 (Table 2). Above 20 µM PEITC and 50 µg/ml BSP (equivalent to 23.5 µM PEITC content), the inhibitory effects measured by gene down-regulation were almost 100% (Table 2). Concentrations between 200 to 1.56 µg/ml (BSP) and 80 to 1 µM (PEITC) were tested to determine the respective dose dependency (Table 2) and $IC_{50}$ values (Table 3) of inhibition of the preparation and the pure compound. Pronounced dose responses for all three genes, further confirmed the validity of the assay and the activity of BSP and PEITC.

The $IC_{50}$ values for COX2 inhibition were 17 μM for PEITC and 38 μg/ml for BSP (containing 17.6 μM PEITC). The $IC_{50}$ values for iNOS inhibition were also comparable for PEITC and BSP and were about four times lower than respective COX2 $IC_{50}$ (Table 3). In the case of IL1β, however, BSP showed somewhat lower $IC_{50}$ as compared to synthetic PEITC (Table 3). The $IC_{50}$ for IL1β in general were several fold lower than those for iNOS and COX2.

TABLE 2

Anti-inflammatory effects of different concentrations of BSP, PEITC, Aspirin and rofecoxib, on the in-vitro gene expression in the LPS-stimulated RAW264.7 macrophages.

| 8 hour treatment (conc.) | COX2 % down-regulation | iNOS % down-regulation | IL1β % down-regulation |
|---|---|---|---|
| BSP μg/ml (PEITC content in μM) | | | |
| 200 (~94.0) | 100.0 ± 0.0 | 99.5 ± 0.7 | 100.0 ± 0.0 |
| 100 (~47.0) | 100.0 ± 0.0 | 100.0 ± 0.0 | 100.0 ± 0.0 |
| 50 (~23.5) | 99.0 ± 0.0 | 99.5 ± 0.7 | 100.0 ± 0.0 |
| 25 (~11.8) | 14.7 ± 21.0 | 91.7 ± 11.0 | 85.7 ± 15.9 |
| 12.5 (~5.8) | −47.5 ± 66.5 | 69.8 ± 20.7 | 70.5 ± 31.0 |
| 3.13 (~1.5) | −78.3 ± 67.2 | 45.7 ± 29.5 | 76.7 ± 15.3 |
| 1.56 (~0.7) | −87.7 ± 64.9 | 38.0 ± 19.2 | 62.0 ± 18.0 |
| PEITC μM | | | |
| 80 | 100.0 ± 0.0 | 99.5 ± 0.7 | 100.0 ± 0.0 |
| 40 | 100.0 ± 0.0 | 99.5 ± 0.7 | 100.0 ± 0.0 |
| 20 | 99.5 ± 0.7 | 99.5 ± 0.7 | 100.0 ± 0.0 |
| 10 | 28.3 ± 15.0 | 81.7 ± 5.5 | 92.0 ± 10.4 |
| 5 | 19.0 ± 27.1 | 69.8 ± 21.1 | 86.0 ± 9.8 |
| 1 | −73.5 ± 20.5 | 2.0 ± 7.1 | 36.5 ± 9.2 |
| rofecoxib μM | | | |
| 20 | 25 | 45 | 15 |
| 10 | 22 | 68 | 12 |
| 5 | 8 | 37 | 10 |
| 1 | −52 | 35 | 18 |
| Aspirin μM | | | |
| 20 | −32 | 40 | 13 |
| 10 | −28 | 29 | 29 |
| 5 | −69 | 17 | 35 |
| 1 | −146 | 12 | 24 |

TABLE 3

$IC_{50}$ of selected anti-inflammatory agents on the expression of the inflammation-related genes in the LPS-stimulated RAW264.7 macrophages.

| compound | $IC_{50}$ in COX2-assay | $IC_{50}$ in iNOS-assay | $IC_{50}$ in IL1β-assay |
|---|---|---|---|
| BSP μg/ml (~PEITC μM) | 38 (~17.6) | 9 (~4.25) | 1.0 (~0.5) |
| PEITC (μM) | 17 | 4 | 2 |

TABLE 4

Effects of PEITC and other isothiocyanates on the expression of the inflammation-related genes in the LPS-stimulated RAW264.7 macrophages.

| 8 HOUR TREATMENT (CONC.) WITH DIFFERENT ISOTHIOCYANATES | COX2 % DOWN-REGULATION | iNOS % DOWN-REGULATION | IL1β % DOWN-REGULATION |
|---|---|---|---|
| PEITC (phenethyl) μM | | | |
| 10 | 28.3 ± 15.0 | 81.7 ± 5.5 | 92.0 ± 10.4 |
| 5 | 19.0 ± 27.1 | 69.8 ± 21.1 | 86.0 ± 9.8 |
| Phenyl (μM) | | | |
| 10 | 3 | 35 | 59 |
| 5 | Up-regulation | 31 | 47 |
| Tert-butyl (μM) | | | |
| 10 | Up-regulation | 0 | 61 |
| 5 | Up-regulation | 3 | 44 |
| Isopropyl μM | | | |
| 10 | Up-regulation | 7 | 59 |
| 5 | Up-regulation | 9 | 40 |
| Allyl μM | | | |
| 10 | ND | ND | ND |
| 5 | Up-regulation | 76 | 86 |

ND = not detectable

For Aspirin and rofecoxib, little inhibition on the gene transcription was observed. When activity of PEITC was compared to those of other forms of isothiocyanates (Table 4), PEITC was by far the most active at both tested concentrations (10 and 5 µM). For IL1β and iNOS, however, the allyl form was found to be equally active as PEITC at 5 µM. A general observation for all in vitro experiments was that at lower concentrations, the experimental fluctuations were greater (Table 2). Also, instead of gene down-regulation, at times genetic up-regulation in the cell was observed (Table 4). A probable explanation for such effect of the test compounds may lie in complex, pleitropic effects of other inter-playing cellular factors such as feed-back mechanisms of genetic regulation within a cell.

COX2 induction in the cell is controlled by two redox-sensitive transcription factors, NFκβ (nuclear factor κβ) and AP1 (Activator protein 1). While LPS-induced 2 expression only requires NFκβ activation, NO-induced COX2 expression requires the activation of both NFκβ and AP1 (von Knethen and Brune, 2000, Biochemistry 39(6):1532-40). AP1 is composed of various proto-oncogene products. Its activation is achieved by superoxides, cytokines, UV irradiation and growth factors (von Knethen et al., 1999, Mol Biol Cell 10(2):361-372).

In our assays, the dose-dependency profile for COX2 was distinct from that of iNOS and IL1β for both PEITC and BSP. In contrast to the sharp decline in the COX2 curve, IL1β, showed only slow changes within the range of concentrations tested (20 µM and 1 µM) (Table 2). In the case of iNOS also, the dose response was gradual until 5 µM point. Apparent selective suppressions of iNOS and IL1β over COX2 at lower concentrations (<20 µM) by BSP and PEITC, are noteworthy since the concentration at which the percentage inhibition attains its maximum (saturation) detectable level (comparing with the control) was found to be same (20 µM) for all the three genes. Hence it is probable, that BSP and PEITC exert a selective NFκβ-mediated inhibitory action on the target genes without exerting any direct effect on AP1-mediated second level of COX2 expression. This is consistent with the cardio-protective function of COX2 in human (Wu et al., 2003, Am. J. Physiol. Heart Circ. Physiol. 285(6):H2420-2429).

At concentrations lower than 20 µM of BSP and PEITC, inhibitions of both iNOS and IL1β were significant but not 100%. Therefore, it is likely that, NO and IL1β acted as additional elicitors of AP1 in the presence of LPS, accounting for the small decline in COX2 mRNA level (Table 2). With BSP and PEITC concentrations of 20 µM and higher, there was a complete absence of any elicitor for AP1. Hence, there was complete inhibitions of the expressions of all the genes (including COX2), most likely mediated by NFκβ (Table 2).

The behavior of COX inhibition by BSP and PEITC was different from that of iNOS and IL1β. It is known that, when activated by LPS, all three pro-inflammatory markers are transcriptionally regulated by nuclear factor κβ (NFκβ) (Baeurerle, 1996, Cell 87(1):13-20; Baldwin, 1996, Annu Rev Immunol 14:649-83; Yamamoto, 2004, Trends Biochem Sci 2004; 29(2):72-9). The COX2 expression is additionally controlled by a second transcription factor, activator protein 1 (AP1), when elicited by LPS in combination with other stimulators such as NO and IL1β (von Knethen and Brune, 2000). Hence, a specific explanation for the observed absence of gradual dose-response in COX2 expression likely lies in a possible dual (NFκβ and AP1 mediated) mode of COX2 activation within the cell. The likelihood of such an assumption is further strengthened by the observation that ~20 µM PEITC/BSP showed saturation of inhibitions for all of the three gene expressions (Table 2). At ≧20 µM of BSP and PEITC, when iNOS and IL1β are completely suppressed, COX2 is totally inhibited as well, indicating the absence of any activity of NFκβ or AP1. At <20 µM of BSP and PEITC, expressions of iNOS and IL1β (and probably also COX2, all NFκβ-mediated) are only partially suppressed, thereby enabling NO and IL1β to act as an elicitor of AP1, in the presence of LPS. This leads to the AP1 activation at <20 µM of PEITC and BSP and hence a second level of COX2 expression, which seems to remain unaffected by either PEITC or BSP (Table 2). It is clear that PEITC and BSP possess novel anti-inflammatory mechanisms of actions that selectively blocks iNOS and IL1β more than COX2 when used below a certain concentration for treatment.

At micromolar concentrations, while BSP and PEITC significantly down-regulated the expression of the marker genes, Aspirin did not (Table 2). At 10-20 µM concentrations of BSP, PEITC and rofecoxib, where cells were incubated for only 6 hours after LPS (1 µg/ml) activation, strong inhibition of gene expressions in response to BSP and PEITC treatments were detected, but not to rofecoxib (Table 2). These observations suggest that BSP and PEITC display novel anti-inflammatory mechanisms of actions that are distinct from both Aspirin and rofecoxib. BSP is capable of preventing the development of inflammation and also can treat pre-inflamed conditions in vivo. This study establishes BSP as an anti-inflammatory agent of therapeutic value. From the results of the study, the involvement of BSP in NFκβ mediated signaling pathway at the transcriptional level is indicated and therapy based on the NFκβ-mediated signaling pathway is contemplated.

All publications and patents mentioned in this document are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention should not be unduly limited to such specific embodiments. Indeed, the contemplated invention includes various modifications of the described compositions and modes for carrying out the invention which are obvious to those skilled in the art or in related fields.

We claim:

1. A method of treating inflammation in a mammal comprising the step of: orally administering to a subject mammal with inflammation a composition comprising ground *Barbarea verna* seed fortified with a therapeutically effective amount of *Barbarea verna* essential oil for treating inflammation.

2. The method of claim 1 wherein the subject has an inflammatory disorder selected from the group consisting of rheumatoid arthritis, asthma, inflammatory bowel disease, Crohn's disease, ulcerative colitis, multiple sclerosis, psoriasis and skin rushes, chronic obstructive pulmonary disease, allergic rhinitis, cardiovascular disease, lupus and metabolic syndrome.

* * * * *